United States Patent [19]
Hofmann et al.

[11] Patent Number: 5,925,044
[45] Date of Patent: Jul. 20, 1999

[54] TROCAR FOR LAPAROSCOPIC OPERATIONS

[75] Inventors: Helge Hofmann, Emmingen; Gernod Fritzsch, Tuttlingen; Wolfram Hill, Freiburg, all of Germany

[73] Assignee: Gebrueder Berchtold GmbH & Co., Tuttlingen, Germany

[21] Appl. No.: 08/884,846

[22] Filed: Jun. 30, 1997

[30] Foreign Application Priority Data

Jul. 1, 1996 [DE] Germany ............................ 196 26 408

[51] Int. Cl.⁶ .................................................. A61B 17/39
[52] U.S. Cl. ................................................ 606/45; 606/46
[58] Field of Search ................................ 606/32, 45, 46, 606/48, 39, 49

[56] References Cited

U.S. PATENT DOCUMENTS

| | | | |
|---|---|---|---|
| 5,273,524 | 12/1993 | Fox et al. .................................. | 604/21 |
| 5,344,420 | 9/1994 | Hilal . | |
| 5,380,291 | 1/1995 | Kaali . | |
| 5,417,687 | 5/1995 | Nardella . | |
| 5,423,809 | 6/1995 | Klicek . | |
| 5,445,142 | 8/1995 | Hassler . | |
| 5,467,762 | 11/1995 | Sauer . | |
| 5,658,280 | 8/1997 | Issa ............................................ | 606/46 |

FOREIGN PATENT DOCUMENTS

| | | |
|---|---|---|
| 0 547 772 A1 | 6/1993 | European Pat. Off. . |
| 0 684 016 A2 | 11/1995 | European Pat. Off. . |
| 41 16 648 A1 | 11/1992 | Germany . |
| 43 08 168 A1 | 9/1993 | Germany . |
| 93 90 139 U | 3/1995 | Germany . |
| WO 93/13718 | 7/1993 | WIPO . |
| WO 94/25110 | 11/1994 | WIPO . |

*Primary Examiner*—Lee Cohen
*Assistant Examiner*—Roy Gibson
*Attorney, Agent, or Firm*—Townsend and Townsend and Crew LLP

[57] ABSTRACT

A trocar for laparoscopic operations on patients has a tube and high frequency connections in the region of the front end of the tube which can be connected to a high frequency generator. A cutting bar is axially displaceable in the tube and can be fixed in a cutting position. The high frequency connections and electrosurgical cutting device connected to the latter are arranged at the front end of the cutting bar.

18 Claims, 2 Drawing Sheets

TROCAR FOR LAPAROSCOPIC OPERATIONS

FIELD OF THE INVENTION

The intention relates to a trocar for laparoscopic operations on patients comprising a tube which is preferably somewhat sharpened at the front and high frequency connections in the region of the front end of the tube, the high frequency connections being connectable to a high frequency generator for the electrosurgical cutting of tissue on penetration of the tube into the patient's body.

DESCRIPTION OF THE PRIOR ART

In a known trocar of this kind (DE 93 90 139 U1) the high frequency electrodes are arranged at the front end of the tube and can be removed, if required, after the introduction of the tube into the patient's body. Apart from the fact that the introduction and removal of the electrodes requires considerable skill on behalf of the surgeon, the effectiveness of the cutting procedure depends in this known trocar on the current-conducting capability of the tissue on which it acts. Thus, the cutting effect varies greatly during the pushing in of the trocar and can hardly be controlled by the surgeon.

Furthermore, it is already known (U.S. Pat. No. 5,380, 921) to introduce an electronic endoscope having a mechanical, transparent tip into a trocar, with the tip forming the insertion passage or puncture passage during the introduction of the trocar into the body. In this instrument, the insertion of the trocar takes place by purely mechanical means, which brings about the danger of hemorrhages.

OBJECT OF THE INVENTION

The object of the invention is to provide a trocar of the initially named kind, by means of which the insertion into the body to be operated on takes place without the danger of hemorrhaging, with a precisely predeterminable cutting action and independently of the electrical resistance of the body tissue.

BRIEF DESCRIPTION OF THE INVENTION

To satisfy this object there is provided a trocar of the initially named kind which is characterized in that a cutting bar is axially displaceable in the tube and can be brought into and fixed in a cutting position, with the high frequency connections and electrosurgical cutting means connected to the latter and heatable by the high frequency current being arranged at the front end of the bar and with the cutting means being located in the cutting position in the region of the front end of the tube.

The concept underlying the invention is thus to be seen in the fact that a special cutting bar is introduced into the trocar tube for the insertion procedure and this cutting bar has special electrosurgical cutting means which can be connected to the high frequency electrodes and which are supplied with high frequency energy by the high frequency or radio frequency generator in such a way that they adopt an ideal temperature for the cutting process. The cutting process is thus largely independent of the electrical resistance of the penetrated tissue and the pronounced heating in the cutting region causes a coagulation of the tissue and thus reduces the danger of hemorrhage.

In a preferred embodiment, the cutting means spans the front end of the cutting bar. As a result, an electrosurgical cutting action is achieved over the entire cross-section of the trocar, and indeed above all when, in a preferred manner, the diameter of the cutting bar is only fractionally less than the inner diameter of the trocar tube and the electrosurgical cutting means extends not only within the cross-section of the cutting bar, but rather also as far as possible up to its marginal edge.

Cutting means which are of elongate design and, in particular, take the form of wires, blades or knives connected to the high frequency connections are particularly preferred. Wires, blades or knives have a good electrosurgical cutting action and, moreover, make it possible for adequate free space to be provided around them permitting a free view of the site of the operation by means of an endoscope which is preferably provided in the area of the front end of the cutting bar.

The pushing in of the trocar is favored when the cutting means, in particular the wires, blades or knives, project in arcuate or pointed manner from the front end of the cutting bar.

When the cutting means, in particular the wires, blades or knives, span the front cross-section of the cutting bar diametrically, or cross-wise or in the manner of a star, then a particularly uniform cutting action is achieved.

A tubular design of the cutting bar such that the front observing end of an endoscope can be accommodated in it directly behind the cutting means is particularly preferred, since in this way an endoscope can be introduced into the interior of the cutting bar by means of which the puncturing process can be followed by the surgeon. Thus, in accordance with the invention, almost the entire inner cross-section of the trocar tube is available for the electrosurgical cutting and for the observation by means of an endoscope.

In this embodiment, a further development in which the cutting means span the free cross-section of the tubular cutting bar ensures a uniform cutting action over the entire bar cross-section. At the same time the view to the cutting point is only trivially hindered by the cutting means.

It is particularly preferred when the front end of the tubular bar is closed off behind the cutting means by a transparent component which is preferably of dome-like design. This makes it possible to protect an endoscope introduced into the tubular cutting bar from vapor or spray contamination.

The cutting means preferably have a spacing from the transparent component which can be maintained by spacers. This makes it possible to ensure that the transparent component which closes off the tubular cutting bar at the front is itself heated to only a small degree by the heated cutting means.

The space between the tube and the cutting bar and/or the inner space of the tubular cutting bar are advantageously connectable to a supply of flushing gas or flushing liquid. The supply of a flushing gas or a flushing liquid from the outside at a suitable position is expedient in counteracting contamination of the endoscope or of the transparent component. For this purpose, carbon dioxide is particularly suitable, which is in any case required during laparoscopic operations to fill the abdominal cavity. However, in the same way, a flushing solution could be used.

The electrosurgical cutting means are preferably fed by high frequency current pulses and it is possible to cut through the tissue layer-wise while viewing it during the puncturing procedure.

A tungsten wire with a diameter of 0.2 mm is, for example, suitable as a wire for the cutting means.

BRIEF LISTING OF THE DRAWINGS

FIG. 1 is an enlarged schematic cross-sectional view of the front end of a trocar in accordance with the invention, with the Figure also showing the front end of an endoscope which has been introduced and, purely schematically, the connection to a high frequency generator and also to a flushing gas supply, FIG. 2 is a sectional view similar to FIG. 1, but of a further embodiment, and FIGS. 3a, 3b and 3c are end views of the tubular cutting bar of FIGS. 1 or 2 with different arrangements of the electrosurgical cutting means.

DESCRIPTION OF THE PREFERRED EMBODIMENTS

Figure 1:
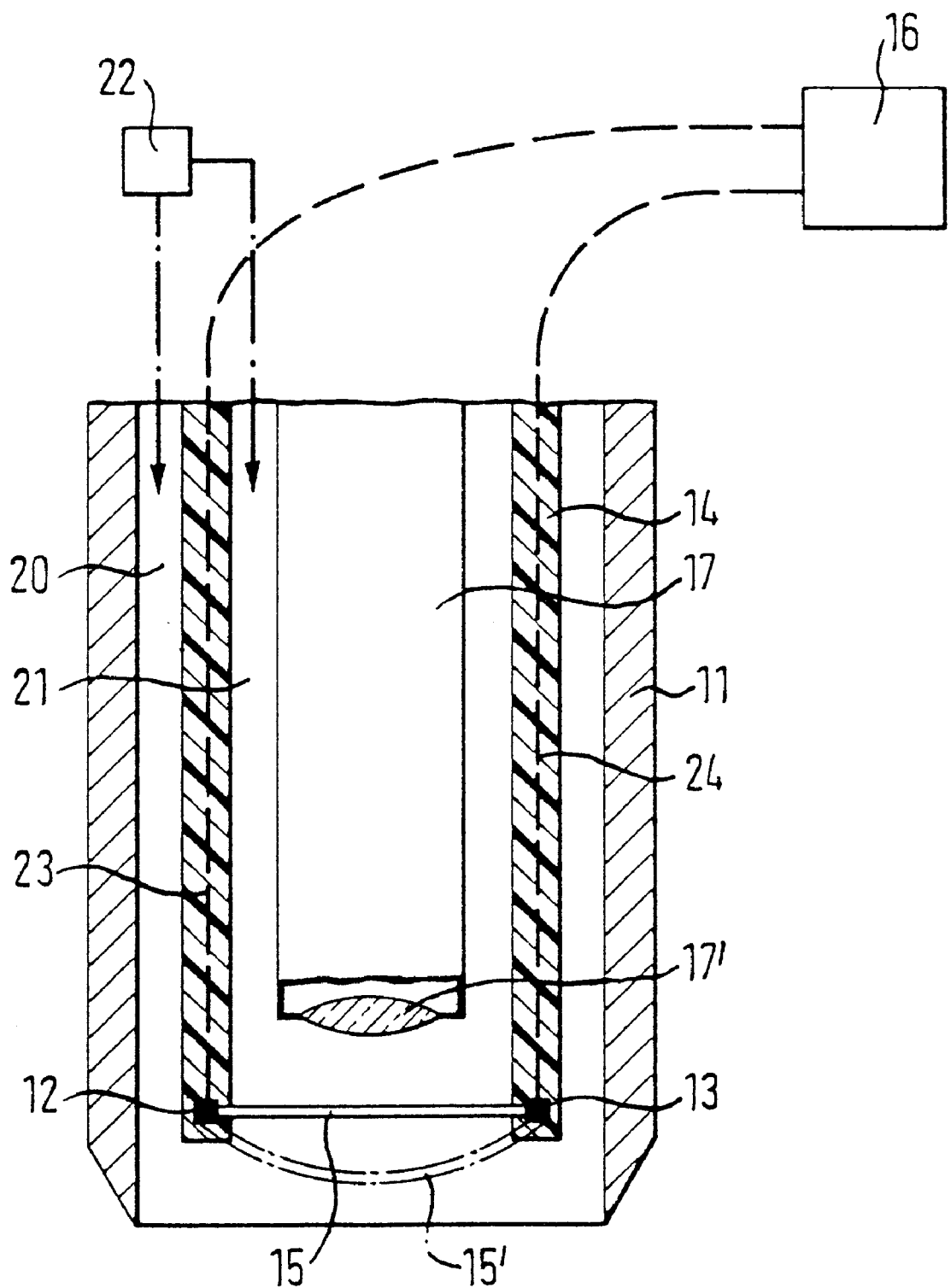

In accordance with FIG. 1 a tubular cutting bar 14 is axially displaceably arranged within a tube 11 of a trocar in accordance with the invention, which is sharpened at the front, so that the front end of the cutting bar is approximately flush with the front end of the tube 11. In FIG. 1 the front end of the cutting bar is set back somewhat relative to the front end of the tube 11, but it can, in a preferred manner, project fractionally beyond the front end of the tube 11. The tubular cutting bar 14 preferably consists of plastic and contains two high frequency feedlines 23 and 24 respectively. These are connected to a high frequency generator 16 and have respective connections 12 and 13 in the region of the front end of the cutting bar 14, between which a cutting wire 15 or alternatively a cutting blade 15' extends. Whereas the cutting wire 15 spans the free cross-section of the cutting bar 14 in a straight line and diametrically (FIG. 3a), the cutting blade 15' projects in arcuate-like manner beyond the front end of the tubular cutting bar 14.

An endoscope 17 is located within the inner space 21 of the tubular cutting bar 14 and has been inserted to such an extent that its observing end 17' is located close to the front opening of the tube-like cutting bar 14 or of the tube 11.

An intermediate space 20 left between the tube 11 and the tubular cutting bar 14 and/or the inner space 21 of the tubular cutting bar 14 is or are connected to a supply 22 of a flushing gas or flushing liquid provided outside of the trocar.

Figure 2:
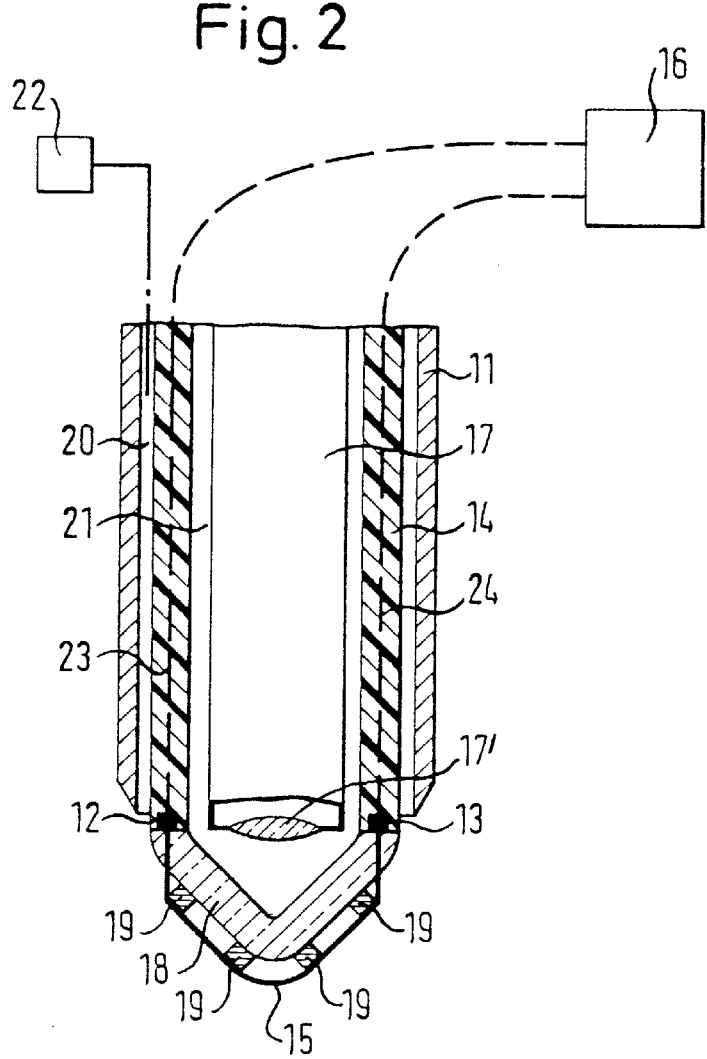

In the embodiment of FIG. 2, in which the same reference numerals designate the same components as in FIG. 1, the front end of the tubular cutting bar 14 is closed by a transparent dome 18, with the cutting wire 15 extending at a distance in front of the dome 18 and being held at a defined spacing from the outer surface of the dome 18 by spacers 19.

The manner of operation of the described trocar is as follows:

Before the penetration into the body of a patient, the tubular cutting bar 14 is brought into one of the positions relative to the trocar tube 11 which can be seen from FIGS. 1 and 2, so that the electrosurgical cutting means 15, 15' is located in the region of the front end of the trocar tube 11.

Thereafter, the endoscope 17 is introduced into the interior of the tubular cutting bar 14, and indeed as close as possible to the electrosurgical cutting means 15, 15' (FIG. 1) or to the transparent dome 18 (FIG. 2) Radiofrequency energy is now applied to the electronic cutting means 15, 15' from the high frequency generator 16, so that these cutting means can adopt a temperature required for the cutting process. The trocar can now be placed onto the body and pushed into the tissue of the body under the decisive cooperation of the electrosurgical cutting means 15, 15'. The puncturing procedure can be observed precisely by the surgeon through the endoscope 17. In this way, the risk of injuring sensitive blood vessels or specific inner organs, such as the intestine, can be reduced quite considerably. Moreover, the electrosurgical cutting procedure ensures that any blood vessels which are eventually cut into are coagulated such that hemorrhages are stopped. The force which needs to be expended for the penetration of the trocar of the invention is considerably reduced relative to known trocars, so that the puncturing procedure can also be carried out substantially more sensitively and with more feeling.

Once the trocar tube 11 has reached the desired position in the body, the endoscope 17 or the tubular cutting bar 14 are removed from the tube 11, whereupon the endoscope 17 is either pushed in on its own anew in order to observe the subsequent surgical procedure, or a suitable medical instrument is introduced into the tube.

In the embodiment of FIG. 1 a flushing gas or a flushing liquid is preferably introduced from the supply 22 into the inner space 21 of the tubular cutting bar 14, because the space between the observing end 17' of the endoscope 17 and the electrosurgical cutting means 15, 15' can then be effectively flushed continuously, and thus a contamination of the observing end 17' of the endoscope 17 is avoided.

In the embodiment of FIG. 2 the supply 22 should in contrast be applied to the intermediate space 20 between the tube 11 and the cutting bar 14, in order to flush the outer surface of the dome 18 in this way, so that contaminations arising during the cutting procedure cannot accumulate there.

Figure 3A:
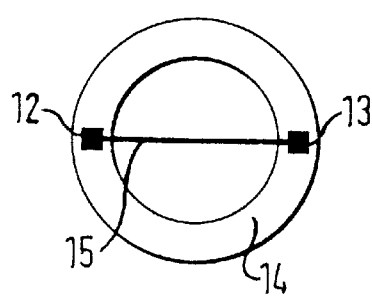

The technically simplest solution for the arrangement of the cutting wire 15 can be found in FIG. 3a. Here, a straight cutting wire 15 is simply diametrically tensioned over the front end of the inner cross-section of the tubular cutting bar 14. The cutting wire is secured in a suitable manner to the diametrically oppositely disposed connections 12, 13.

Figure 3B:
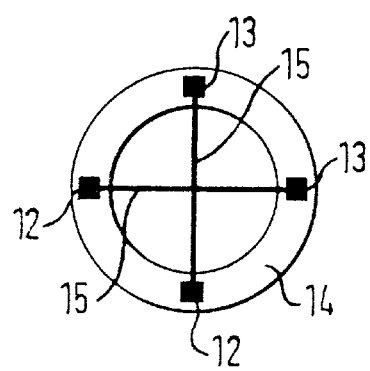

In the cross-like arrangement of two cutting wires 15 in accordance with FIG. 3b, a more uniform cutting action is ensured over the cross-section of the cutting bar 14 In this case, however, two connection pairs 12, 13 must be provided and must be displaced relative to one another angularly by 90°.

Figure 3C:
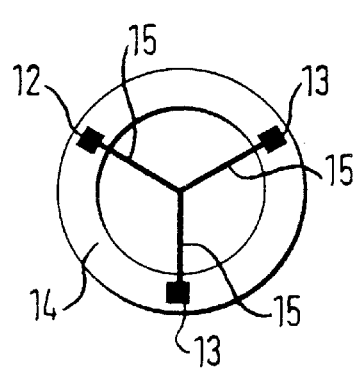

Furthermore, a three-pointed star arrangement of the cutting wire 15 is conceivable in accordance with FIG. 3c, for which purpose three connections 12, 13, 13 are to be arranged displaced by an angle of 120° relative to one another at the end face of the tubular cutting bar 14.

What is claimed is:

1. A trocar for a laparoscopic operation on a patient, comprising:

a tube having a front end;

a plurality of high frequency connections disposed in a region of the front end of the tube, the high frequency connections being connectable with a high frequency generator for receiving a high frequency current therefrom;

a cutting bar which is axially displaceable in the tube and is fixable in a cutting position, the cutting bar having a front end; and electrosurgical cutting means arranged at the front end of the cutting bar and connected with the plurality of high frequency connections to be heated by the high frequency current for electrosurgically cutting tissue on penetration of the tube into the patient's body, the electrosurgical cutting means being located in a region of the front end of the tube in the cutting position, wherein the cutting bar is of a tubular design to define an inner space therein such that an endoscope is receivable into the inner space of the cutting bar to place a front observing end of the endoscope directly behind the electrosurgical cutting means, and wherein the cutting bar is radially spaced from the tube to define a space therebetween so as to allow a flushing gas or a flushing liquid to be introduced to at least one of the inner space of the cutting bar and the space between the cutting bar and the tube to prevent contamination of the observing end of the endoscope during the cutting of the tissue.

2. A trocar in accordance with claim 1 wherein the tube is sharpened at the front end.

3. A trocar in accordance with claim 1 wherein the cutting bar includes a transparent end portion enclosing the front end thereof, the transparent end portion being disposed behind the electrosurgical cutting means.

4. A trocar in accordance with claim 3 wherein the transparent end portion of the cutting bar has an inner surface facing toward the inner space of the cutting bar and an outer surface facing away from the inner space of the cutting bar, and wherein the cutting bar and the tube are configured so as to allow a flushing gas or a flushing liquid to be introduced to the space between the cutting bar and the tube to prevent contamination of the outer surface of the transparent end portion of the cutting bar.

5. A trocar in accordance with claim 3 wherein the transparent end portion of the cutting bar comprises a transparent dome.

6. A trocar in accordance with claim 3 further comprising a plurality of spacers disposed between the inner surface of the transparent end portion of the cutting bar and the electrosurgical cutting means to maintain a spacing between the transparent end portion and the electrosurgical cutting means.

7. A trocar in accordance with claim 1 wherein the electrosurgical cutting means spans the front end of the cutting bar.

8. A trocar in accordance with claim 1 wherein the electrosurgical cutting means are of elongate design.

9. A trocar in accordance with claim 8 wherein the electrosurgical cutting means comprises wires, blades or knives which are connected with the plurality of high frequency connections.

10. A trocar in accordance with claim 8 wherein the electrosurgical cutting means project in an arcuate-like manner or in a pointed manner from the front end of the cutting bar.

11. A trocar in accordance with claim 8 wherein the electrosurgical cutting means span a front cross-section of the front end of the cutting bar diametrically.

12. A trocar in accordance with claim 8 wherein the electrosurgical cutting means span a front cross-section of the front end of the cutting bar in a cross-wise manner.

13. A trocar in accordance with claim 8 wherein the electrosurgical cutting means span a front cross-section of the front end of the cutting bar in a star-like manner.

14. A trocar in accordance with claim 1 wherein the cutting bar and the tube are configured so as to allow a flushing gas or a flushing liquid to be introduced to both the inner space of the cutting bar and the space between the cutting bar and the tube.

15. A method for performing a laparoscopic operation on a patient, comprising:

providing a tube having a front end;

providing a plurality of high frequency connections in a region of the front end of the tube;

connecting the high frequency connections with a high frequency generator for receiving a high frequency current therefrom;

inserting a tubular cutting bar axially into the tube and fixing the cutting bar in a cutting position so as to define an inner space in the tubular cutting bar and a radial space between the cutting bar and the tube;

arranging electrosurgical cutting means at the front end of the cutting bar and connecting the electrosurgical cutting means with the plurality of high frequency connections to heat the electrosurgical cutting means with the high frequency current;

inserting an endoscope into the inner space of the cutting bar to place a front observing end of the endoscope directly behind the electrosurgical cutting means;

penetrating the tube into the patient's body for electrosurgically cutting tissue with the electrosurgical cutting means; and introducing a flushing gas or a flushing liquid to at least one of the inner space of the cutting bar and the space between the cutting bar and the tube in a manner so as to prevent contamination of the observing end of the endoscope during the cutting of the tissue.

16. A method in accordance with claim 15 further comprising enclosing the front end of the cutting bar with a transparent end portion and locating the transparent end portion behind the electrosurgical cutting means.

17. A method in accordance with claim 16 wherein the transparent end portion of the cutting bar has an inner surface facing toward the inner space of the cutting bar and an outer surface facing away from the inner space of the cutting bar, and wherein the step of introducing a flushing gas or a flushing liquid comprises introducing the flushing gas or the flushing liquid to the space between the cutting bar and the tube to prevent contamination of the outer surface of the transparent end portion of the cutting bar.

18. A method in accordance with claim 15 wherein the step of introducing a flushing gas or a flushing liquid comprises introducing the flushing gas or the flushing liquid to both the inner space of the cutting bar and the space between the cutting bar and the tube.

* * * * *